United States Patent [19]

Ogawa et al.

[11] Patent Number: 5,652,272

[45] Date of Patent: Jul. 29, 1997

[54] OPHTHALMIC PREPARATIONS FOR REDUCING INTRAOCULAR PRESSURE

[75] Inventors: Takahiro Ogawa; Takaaki Deguchi, both of Hyogo, Japan

[73] Assignee: Senju Pharmaceutical Co., Ltd., Osaka, Japan

[21] Appl. No.: 404,315

[22] Filed: Mar. 15, 1995

[30] Foreign Application Priority Data

Mar. 18, 1994 [JP] Japan .................................. 6-087170

[51] Int. Cl.$^6$ .................................................. A67K 31/14
[52] U.S. Cl. .......................................... 514/652; 514/913
[58] Field of Search ................................... 514/652, 913

[56] References Cited

FOREIGN PATENT DOCUMENTS 0398326  11/1990  European Pat. Off. .

OTHER PUBLICATIONS

British Journal of Ophthalmology—"Effect of Topical Ketanserin . . . Pressure", pp. 344–348, 1993.
Journal of Ocular Pharmacology—"Effect of Serotonin . . . ", Krootila, et al, pp. 279–290, 1987.
Drugs of the Future 1992, 17(12): 1093–1096—"Sarpogrelate Hydrochloride".
3390–377—Abstract—"The Effect of Anplag . . . Glaucoma Patients", M. Takenaka et al., 1995.
3322–309—Abstract—"The Effect of Anplac . . . Intraocular Pressure in Rabbits", T. Mano et al., 1995.
Journal of Pharmacobio–Dynamics—vol. 14, No. 4, Apr. 1991 pp. 177–181.

*Primary Examiner*—Zohreh Fay
*Attorney, Agent, or Firm*—Burgess, Ryan & Wayne

[57] ABSTRACT

The present invention provides an ophthalmic preparation for reducing intraocular pressure comprising 2-[3-dimethylamino-2-(2-carboxyethoxy)propionyloxy]-2'-methoxybibenzyl or a salt thereof, which preparation exhibits intraocular pressure reducing activity, without exerting effects on the central nervous system, and can advantageously be used as a prophylactic and therapeutic agent for ocular hypertension and glaucoma bringing about elevated intraocular pressure.

2 Claims, No Drawings

OPHTHALMIC PREPARATIONS FOR REDUCING INTRAOCULAR PRESSURE

This invention relates to ophthalmic preparations comprising sarpogrelate or a salt thereof which exhibit excellent intraocular pressure reducing activity.

Glaucoma, being heretofore considered an important problem in the field of ophthalmology, refers to the symptoms characterized by elevation of intraocular pressure over the normal range of 10 to 20 mmHg and manifestation of impaired visual function and is regarded as one of intractable ophthalmologic diseases. Currently, glaucoma is treated with the aim to control intraocular pressure. Referring to the pharmacotherapy of glaucoma, cholinergic drugs being represented by pilocarpine and anticholinesterase agents have long been employed as an ophthalmic preparation. However, these drugs exhibit strong side effects, such as feeling of blackness and ocular injection due to miosis, as well as iridocystoma, synechia of iris, cataractogenesis, retinal detachment and so on being associated with long-term consecutive application. Sympathomimetic drugs such as epinephrine and dipivefrin, with their intraocular pressure reducing activities, have also been put in clinical use, but suffer from the disadvantages such as their limited indication to open-angle glaucoma as well as accompaniment of mydriasis, blepharitis, conjunctival pigmentation, and other systemic adverse effects such as increased heart rate and elevated blood pressure. In recent years, β-blockers such as timolol, pindolol and carteolol, which, upon instillation to the eye, act to reduce intraocular pressure through their suppression of production of aqueous humor and offer the advantage of being free from effects on the pupil, have been used widely. However, these drugs also are defective in that they are liable to cause a feeling of dryness, allergic blepharitis and superficial keratitis locally in the eye. As the only one intraocular-pressure reducing agent for systemic administration, there are available carbonic anhydrase inhibitors such as acetazolamide and methazolamide, but these drugs are known to cause gastrointestinal disorders, urolithiasis and electrolyte abnormality, as well. Moreover, a report was published on the possibility that angiotensin converting enzyme inhibitors and angiotensin II antagonists, which inhibit the renin-angiotensin system governing the control of blood pressure, could be utilized as a glaucoma treatment agent, but none of these has reached the stage of commercialization for clinical application.

It was recently reported that 3-[2-4-fluorobenzoyl)-1-piperidinyl]ethyl]-2,4(1H,3H)-quinazolinedione (generic name: ketanserin), which blocks selectively serotonin (5-HT$_2$) receptor, reduces intraocular pressure in both eyes simultaneously when applied topically to one eye (Journal of Ocular Pharmacology, vol. 3, No. 4, pp. 279 to 291, 1987).

Furthermore, Japanese Unexamined Patent Publication No. Hei 2-304022 describes that a specifically determined type of (3-aminopropoxy)bibenzyl compounds, despite their basic difference from ketanserin in chemical structure, exhibit serotonin antagonistic activity and by virtue of this, inhibit thrombus formation and also suppress vasoconstriction, thus being particularly effective in ameliorating and improving various microcirculation disorders brought about by thrombus formation and vasoconstriction in cerebral circulatory impairments, ischemic heart diseases, peripheral circulatory disturbances and the like, but the description is not given on their intraocular-pressure reducing effect.

In developing a pharmaceutical preparation for topical ophthalmic application, special attention must be paid to insure that such preparation will produce efficacy at the site of ocular instillation alone (to have local action) without involvement of the systemic circulatory system and central nervous system and desirably will neither affect any region other than the lesioned tissue nor exert any systemic effect. Accordingly, there is demanded the development of a pharmaceutical preparation for ophthalmologic use that possesses local action, produces lessened side-effects and permits the safe application to be realized.

In view of the above, the present inventors performed screening of various compounds in search for a 5-HT$_2$ receptor antagonist that would meet the condition of producing an intraocular-pressure reducing effect at the site of administration alone and as a result, discovered that, among the (3-aminopropoxy)bibenzyl compounds described in the above-mentioned Japanese Unexamined Patent Publication No. Hei 2-304022, sarpogrelate (generic name: sarpogrelate; hereinafter referred to in some instances as "sarpogrelate") or its hydrochloride (generic name: sarpogrelate hydrochloride; hereinafter referred to in some instances as "sarpogrelate hydrochloride") unexpectedly exhibits, upon instillation to the eye, improved intraocular-pressure reducing activity and is free from the shortcomings as mentioned previously., thereby leading to completion of the present invention.

Thus, this invention relates to:
(1) Ophthalmic preparations for reducing intraocular pressure which comprise sarpogrelate (i.e. sarpogrelate) or a salt thereof,
(2) Ophthalmic preparations for reducing intraocular pressure as described under the item (1), wherein the salt of sarpogrelate is sarpogrelate hydrochloride (i.e. sarpogrelate hydrochloride), and
(3) Ophthalmic preparations for reducing intraocular pressure as described under the item (2), wherein the concentration of 2-[3-dimethylamino-2-(2-carboxyethoxy) propionyloxy]-2'methoxybibenzyl hydrochloride (i.e. sarpogrelate hydrochloride) is the range of 0.1 to 5.0 (w/v) %.

As the salt of sarpogrelate, which is usable in this invention, there are employed their pharmacologically acceptable salts, such as salts with inorganic acids being exemplified by hydrochloride, hydrobromide, sulfate, nitrate and phosphate and salts with organic acids being exemplified by acetate, citrate, tartrate, fumarate, maleate, toluenesulfonate and methanesulfonate, with its hydrochloride (i.e. sarpogrelate hydrochloride) among others being preferable. sarpogrelate or their salts, which are useful in the present invention, can be produced for example by the process described in Japanese Patent Publication No. Sho 63-13427 or other processes similar thereto.

The ophthalmic preparation for reducing intraocular pressure according to the present invention can be manufactured by incorporating sarpogrelate or a salt thereof therein.

The ophthalmic preparation for reducing intraocular pressure can be provided in any pharmaceutical dosage forms that are conventionally used as an ophthalmic preparation, such as aqueous ophthalmic preparations being exemplified by aqueous ophthalmic solution, aqueous suspended ophthalmic solution, viscous ophthalmic solution and solubilized ophthalmic solution, and non-aqueous ophthalmic preparations being exemplified by non-aqueous ophthalmic solution and non-aqueous suspended ophthalmic solution.

When the ophthalmic preparation for reducing intraocular pressure according to the present invention is processed in the form of an aqueous ophthalmic solution, it is desirable to incorporate the additives which are conventionally used in aqueous ophthalmic solutions. As the additives, there are used for example preservatives, isotonizing agents, buffers, stabilizers or pH adjusting agents and the like.

As a preservative, there are employed parabens (e.g., methyl p-hydroxybenzoate, propyl p-hydroxybenzoate, etc.), invert soaps (e.g., benzalkonium chloride, benzethonium chloride, chlorhexidine gluconate, cetylpyridinium chloride, etc.), alcohol derivatives (e.g., chlorobutanol, phenethyl alcohol, benzyl alcohol, etc.), organic acids and their salts (e.g., sodium dehydroacetate, sorbic acid and its salts), phenols (e.g., p-chloromethoxyphenol, p-chloro-m-cresol, etc.), and organomercury compounds (e.g. thimerosal, phenylmercuric nitrate, nitromesol, etc.).

As an isotonizing agent, for example, use is made of sodium chloride, sorbitol, mannitol, glycerol and so on, while examples of the buffer as employed include phosphates, borates, citrates, acetates and amino acid salts, and as a stabilizer, there are used for example disodium edetate, sodium citrate, sodium polyphosphate, and sulfurous acid salts. The pH adjusting agent used includes for example hydrochloric acid, acetic acid, sodium hydroxide and phosphoric acid.

In addition, the ophthalmic preparation can also be processed by suitably formulating water-soluble high-molecular compounds, surfactants, etc. As a water-soluble high-molecular compound, for example, there are used cellulose derivatives, vinylic high-molecular compounds and polyhydric alcohol compounds. Examples of the cellulose derivative as used include alkyleelluloses being exemplified by methylcellulose and carboxymethylcellulose, and hydroxyalkylcelluloses being exemplified by hydroxypropylcellulose and hydroxyethyl-cellulose, and as a vinylic high-molecular compound, for example, use is made of polyvinylpyrrolidone, polyvinyl alcohols, polymers and ethylene-maleic anhydride copolymers, while as a polyhydric alcohol, for example, there may be used polyethylene glycol and propylene glycol. The surfactant as used includes for example nonionic surfactants being exemplified by polysorbate and polyoxyethylene hydrogenated castor oil, cationic surfactants being exemplified by quaternary ammonium salts, and anionic surfactants being exemplified by alkyl sulfates, and amphoteric surfactants being exemplified by lecithins.

In cases where the ophthalmic preparation of the present invention is processed into the dosage form of an aqueous suspended ophthalmic solution, there are used suspending agents which are conventionally utilized in aqueous suspended ophthalmic solutions. As such suspending agents, there are used methylcellulose, carboxymethylcellulose, carboxyvinyl polymers, hydroxypropylmethylcellulose, polyvinyl alcohols, polyvinylpyrrolidones, macrogols (polyethylene glycols), sodium chondroitin sulfate, polysorbate 80 and so on.

The ophthalmic preparation of the present invention is advantageously used after being adjusted to a pH range which is conventionally adopted for topical application to the eye, and is normally employed after being adjusted to pH 3 to 8, preferably pH 4 to 6. For the pH adjustment, hydrochloric acid, acetic acid, sodium hydroxide, etc. can be used.

The ophthalmic solution of the present invention is used after being adjusted to an osmotic pressure range which is conventionally adopted for topical application to the eye, and is normally employed after being adjusted to 230 to 450 mOsm, preferably 260 to 320 mOsm. For this adjustment, sodium chloride, boric acid, glycerin, mannitol, etc. can be employed.

Unless contrary to the objective of this invention, the ophthalmic solution of the present invention may suitably be formulated with other medicinally active agents, in addition to sarpogrelate or a salt thereof.

The concentration of sarpogrelate or a salt thereof in the aqueous preparation for reducing intraocular pressure according to the present invention varies depending upon the route of administration, symptoms of the patient and the like, but in the case of the utilization in adult patients as an ophthalmic solution, the compound normally is processed into a preparation of a concentration in the range of 0.1 to 5.0 (w/v) %, which is preferably administered such patients through topical application to the eye three to six times a day at a single dose of one to several drops.

Described in the following are experiment example and examples to illustrate the present invention in more detail and to demonstrate the effects of this invention. It should be understood, however, that these are merely illustrative and the present invention is by no means limited by them.

EXPERIMENT EXAMPLE 1

Test in rabbits on the intraocular pressure reducing effect
Test substance:

Used as a test substance was sarpogrelate hydrochloride as dissolved in isotonic saline to a concentration of 1.0 (w/v) % and adjusted to pH 7.0. (hereinafter referred to as 1.0% ophthalmic solution of sarpogrelate hydrochloride). Test method:

Pigmented rabbits weighing about 2 kg and having no abnormality observed in the ocular anterior chamber were subjected to measurement of intraocular pressure with use of Pneumatonograph (manufactured by Alcon Co. of U.S.A.) twice 0.5 hour and immediately before topical application of the test substance, and three pigmented rabbits which showed stable intraocular pressure were utilized in the test. The above-mentioned 1.0% ophthalmic solution was applied topically in 50 μl portions to the right eye of each of these rabbits, with isotonic saline being applied to the left eye as a control, and measurement of intraocular pressure was taken for both eyes 0.5, 1, 2 and 4 hours after the topical application, with the intraocular-pressure measurement immediately before topical application being taken as an initial value. Results:

The results are shown in Table 1 (group treated through topical application of 1.0% ophthalmic solution of sarpogrelate hydrochloride) and Table 2 (group treated through topical application of isotonic saline). As is evident from the results shown in Tables 1 and 2, no variation in intraocular pressure was observed in the left eyes of the group treated through topical application of isotonic saline, whereas reductions in intraocular pressure were noted in the right eyes in the group treated through topical application of 1.0% ophthalmic solution of sarpogrelate hydrochloride.

TABLE 1

Intraocular pressure measurements

| Animal group | Intraocular pressure, mmHg Time after treatment, hrs | | | | |
|---|---|---|---|---|---|
| | 0 | 0.5 | 1 | 2 | 4 |
| Test animal A | 23.0 | 22.0 | 21.5 | 20.5 | 20.0 |
| Test animal B | 23.0 | 22.0 | 21.0 | 21.0 | 20.0 |
| Test animal C | 25.0 | 23.0 | 23.0 | 22.0 | 21.0 |
| Mean | 23.7 | 22.3 | 21.8 | 21.2 | 20.3 |

TABLE 2

| | Intraocular pressure measurements | | | | |
|---|---|---|---|---|---|
| | Intraocular pressure, mmHg Time after instillation, hrs. | | | | |
| Animal group | 0 | 0.5 | 1 | 2 | 4 |
| Test animal A | 22.5 | 23.0 | 22.5 | 21.0 | 21.0 |
| Test animal B | 25.0 | 25.0 | 24.0 | 25.0 | 24.0 |
| Test animal C | 25.0 | 26.0 | 26.0 | 26.0 | 25.0 |
| Mean | 24.2 | 24.7 | 24.2 | 24.0 | 23.3 |

Example 1

Aqueous ophthalmic solution

An aqueous ophthalmic solution was prepared in accordance with the following formulation:

| | |
|---|---|
| Sarpogrelate hydrochloride | 1.0 g |
| Sodium acetate | 0.05 g |
| Benzalkonium chloride | 0.005 g |
| Sodium chloride | 0.65 g |
| Sodium hydroxide | q.s. |
| Diluted hydrochloric acid | q.s. |
| Distilled water | To make the total up to 100 ml (pH 5.0) |

Example 2

Aqueous suspended ophthalmic solution

An aqueous suspended ophthalmic solution was prepared in accordance with the following formulation:

| | |
|---|---|
| Sarpogrelate hydrochloride | 2.5 g |
| Concentrated glycerin | 2.6 g |
| Disodium dihydrogenphosphate | 0.5 g |
| Polysorbate 80 | 0.1 g |
| Benzalkonium chloride | 0.005 g |
| Diluted hydrochloric acid | q.s. |
| Sodium hydroxide | q.s. |
| Distilled water | To make the total up to 100 ml (pH 7.0) |

We claim:

1. A method for reducing intraocular pressure which comprises applying topically to the eyes of a human subject in need thereof an ophthalmic preparation comprising sarpogrelate or a salt.

2. A method for treating glaucoma or ocular hypertension which comprises applying topically to the eyes of a patient with glaucoma or ocular hypertension an ophthalmic preparation comprising sarpogrelate or a salt.

* * * * *